United States Patent
Zhong et al.

(10) Patent No.: US 11,524,177 B2
(45) Date of Patent: Dec. 13, 2022

(54) MULTI-LEAF COLLIMATOR AND RADIOTHERAPY EQUIPMENT

(71) Applicants: OUR UNITED CORPORATION, Xi'an (CN); SHENZHEN OUR NEW MEDICAL TECHNOLOGIES DEVELOPMENT CO., LTD., Shenzhen (CN)

(72) Inventors: Ming Zhong, Xi'an (CN); Huiliang Wang, Xi'an (CN); Yueming Yang, Xi'an (CN)

(73) Assignees: Our United Corporation, Xi'an (CN); Shenzhen Our New Medical Technologies Development Co., Ltd., Shenzhen (CN)

(*) Notice: Subject to any disclaimer, the term of this patent is extended or adjusted under 35 U.S.C. 154(b) by 0 days.

(21) Appl. No.: 17/047,038

(22) PCT Filed: Apr. 11, 2019

(86) PCT No.: PCT/CN2019/082214
§ 371 (c)(1),
(2) Date: Oct. 12, 2020

(87) PCT Pub. No.: WO2019/196897
PCT Pub. Date: Oct. 17, 2019

(65) Prior Publication Data
US 2021/0187322 A1  Jun. 24, 2021

(30) Foreign Application Priority Data
Apr. 12, 2018  (CN) .......................... 201810327686.3

(51) Int. Cl.
*A61N 5/10*  (2006.01)
*G21K 1/04*  (2006.01)

(52) U.S. Cl.
CPC ........... *A61N 5/1045* (2013.01); *G21K 1/046* (2013.01)

(58) Field of Classification Search
CPC .......... A61B 6/06; A61N 5/10; A61N 5/1042; A61N 5/1045; G21K 1/02; G21K 1/04;
(Continued)

(56) References Cited

U.S. PATENT DOCUMENTS

2004/0240621 A1   12/2004   Noguchi
2017/0128746 A1*  5/2017   Zwart .................. A61N 5/1045

FOREIGN PATENT DOCUMENTS

CN   103272338 A   9/2013
CN   204745394 U   11/2015
(Continued)

OTHER PUBLICATIONS

International Search Report and Written Opinion of PCT Application PCT/CN2019/082214—17 pages (dated Jun. 20, 2019).
(Continued)

*Primary Examiner* — Anastasia Midkiff
(74) *Attorney, Agent, or Firm* — Knobbe, Martens, Olson & Bear, LLP

(57) ABSTRACT

A multi-leaf collimator includes a first carriage, a second carriage, a drive device, a first set of leaves disposed on the first carriage, and a second set of leaves disposed on the second carriage, wherein the first set of leaves and the second set of leaves are disposed oppositely to each other, and each leaf in each of the sets of leaves is movable relative to each respective carriage; and the drive device is configured to drive the first carriage and the second carriage to move in the same direction synchronously.

12 Claims, 2 Drawing Sheets

(58) Field of Classification Search
CPC .............. G21K 1/046; G01N 2223/316; G01N 2223/32; G01N 2223/321
See application file for complete search history.

(56) References Cited

FOREIGN PATENT DOCUMENTS

| CN | 108379749 A   | 8/2018 |              |
|----|---------------|--------|--------------|
| CN | 208678192 U * | 4/2019 | ...... A61N 5/10 |
| CN | 208678192 U   | 4/2019 |              |

OTHER PUBLICATIONS

First Office Action of Chinese application No. 201810327686.3—11 pages (dated Jun. 21, 2019).
Second Office Action of Chinese application No. 201810327686.3—11 pages (dated Dec. 31, 2019).
Notification to Grant Patent Right for Invention of Chinese application No. 201810327686.3—3 pages (dated Mar. 5, 2002).

* cited by examiner

MULTI-LEAF COLLIMATOR AND RADIOTHERAPY EQUIPMENT

CROSS-REFERENCE TO RELATED APPLICATIONS

The present disclosure is a national phase application of PCT International Application No. PCT/CN2019/082214, filed on Apr. 11, 2019, which claims priority to Chinese Patent Application No. 201810327686.3, filed on Apr. 12, 2018 and entitled "MULTI-LEAF COLLIMATOR AND RADIOTHERAPY DEVICE", the contents of which are incorporated herein by reference in their entireties.

TECHNICAL FIELD

The present disclosure relates to the field of radiotherapy, in particular relates to a multi-leaf collimator and a radiotherapy equipment.

BACKGROUND

A multi-leaf collimator (MLC), which is a mechanical movement part, is used for generating a conformal radiation field and plays an important role in a radiotherapy equipment. Generally, the MLC includes two carriages that are oppositely disposed. Each of the carriages is provided with a set of leaves. The two set of leaves respectively disposed on the two carriages are movable relative to the carriage in a longitudinal direction of the leaf, such that the irradiation field in a shape corresponding to the shape of a tumor target area (that is, the shape of a tumor to be irradiated) is formed.

SUMMARY

Embodiments of the present disclosure provide a multi-leaf collimator and a radiotherapy equipment. The technical solutions are as follows.

According to a first aspect of the embodiments of the present disclosure, a multi-leaf collimator is provided. The multi-leaf collimator includes:

a first carriage, a second carriage, a drive device, a first set of leaves disposed on the first carriage, and a second set of leaves disposed on the second carriage; wherein the first set of leaves and the second set of leaves are disposed oppositely to each other, and each leaf in each of the sets of leaves is movable relative to the carriage; and the drive device is configured to drive the first carriage and the second carriage to move in the same direction synchronously.

Optionally, the first carriage is provided with a carriage end, a load-bearing end, and a first light-transmitting hole between the carriage end and the load-bearing end; wherein the carriage end is configured to mount the first set of leaves;

the second carriage is disposed at the load-bearing end; and the drive device is connected to the first carriage, and configured to drive the first carriage to move, such that the first carriage drives the second carriage to move in the same direction synchronously.

Optionally, the multi-leaf collimator further includes a base; wherein the first carriage is disposed on the base, and the base is provided with a second light-transmitting hole; and an orthographic projection of the first light-transmitting hole on the base covers an area where the second light-transmitting hole is disposed.

Optionally, the multi-leaf collimator further includes a drive motor disposed on the second carriage, and configured to drive the second carriage to move.

Optionally, the first carriage and the second carriage are disposed oppositely to each other, and the multi-leaf collimator further includes a first differential and a second differential; wherein the first differential is connected to the first carriage, and the second differential is connected to the second carriage; and the drive device is connected to the first differential and the second differential respectively, and configured to drive the first differential and the second differential such that the first carriage and the second carriage move in the same direction synchronously.

Optionally, the multi-leaf collimator further includes: a main drive shaft, and a first transmission gear and a second transmission gear that are engaged with each other; wherein the drive device is connected to the first transmission gear, and the second transmission gear is sleeved on the main drive shaft; and one end of the main drive shaft is connected to the first differential, and the other end of the main drive shaft is connected to the second differential.

Optionally, the multi-leaf collimator meets at least one of the following conditions:

both the first differential and the second differential are planetary differentials; and both the first transmission gear and the second transmission gear are bevel gears.

Optionally, the multi-leaf collimator further includes: a field control motor, and a third differential connected to the field control motor; wherein the third differential is connected to the first differential and the second differential respectively, and configured to drive the first differential and the second differential under the drive of the field control motor, such that the first carriage and the second carriage move toward or distally from each other.

Optionally, the multi-leaf collimator further includes: a third transmission gear and a fourth transmission gear; wherein a transmission shaft of the third differential is connected to the field control motor;

a first output shaft of the third differential is connected to the third transmission gear, and the third transmission gear is engaged with a main transmission gear in the first differential; and a second output shaft of the third differential is connected to the fourth transmission gear, and the fourth transmission gear is engaged with a main transmission gear in the second differential.

According to a second aspect of the embodiments of the present disclosure, a radiotherapy equipment including the multi-leaf collimator as described in the first aspect is provided.

It should be understood that the above general description and the following detailed description are only examples and cannot limit the present disclosure.

BRIEF DESCRIPTION OF DRAWINGS

For clearer descriptions of the technical solutions in the embodiments of the present disclosure, the following briefly introduces the accompanying drawings required for describing the embodiments. Apparently, the accompanying drawings in the following description show merely some embodiments of the present disclosure, and persons of ordinary skill in the art may also derive other drawings from these accompanying drawings without creative efforts.

The drawings herein are incorporated into the specification and constitute a part of the specification, show embodiments in accordance with the disclosure, and are configured to explain the principle of the disclosure together with the specification.

DESCRIPTION OF EMBODIMENTS

For clearer descriptions of the objectives, technical solutions, and advantages of the present disclosure, the embodiments of the present disclosure are further described in detail in combination with the accompanying drawings. Obviously, the described embodiments are only a part of the embodiments of the present disclosure, rather than all of them. Based on the embodiments in the present disclosure, all other embodiments obtained by those of ordinary skill in the art without creative work shall fall within the protection scope of the present disclosure.

Radiotherapy is an important technical means for tumor treatment. However, during radiotherapy, breathing of a patient may cause shift of the position of the tumor target area. In this case, the irradiation field formed by the MLC cannot be accurately aligned to the tumor target area. In example implementations, methods such as respiratory depression, respiratory gating, or autonomous breathing control may be adopted to address situations that the irradiation field cannot be accurately aligned with the tumor target area due to the position shift of the tumor target area caused by the patient's breathing. The autonomous breathing control may control the movement of the position of the irradiation field by adjusting the position of a treatment couch, or adjusting the position of a leaf disposed on each MLC, or respectively controlling the movement of the two carriages in the MLC.

However, during adjusting the positions of leaves disposed on each MLC separately, or controlling the movement of the two carriages separately, the leaves are subject to collisions in the case that the gap between the two set of leaves is small, due to the control accuracy and control errors, which may damage the drive mechanism of the leaf. Moreover, none of the above adjustment methods can ensure that the shape of the irradiation field is invariant when the position of the irradiation field changes, and thus the accuracy and the reliability are low.

Figure 1:
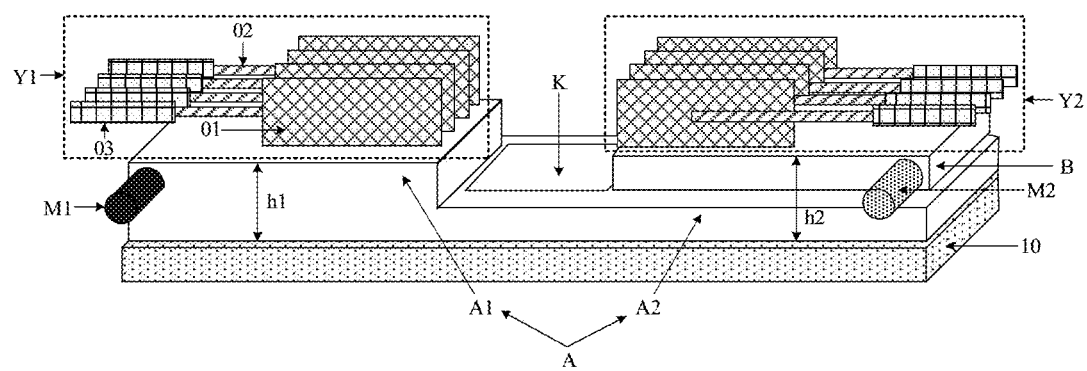
FIG. 1 is a schematic structural diagram of a multi-leaf collimator according to an embodiment of the present disclosure.

FIG. 1 is a schematic structural diagram of a multi-leaf collimator according to an embodiment of the present disclosure, which can address low accuracy of the multi-leaf collimator in tracking tumor target areas. The multi-leaf collimator may also be called a multi-leaf diaphragm. As shown in FIG. 1, the multi-leaf collimator may include a first carriage A, a second carriage B, a drive device M1, a first set of leaves Y1 disposed on the first carriage A, and a second set of leaves Y2 disposed on the second carriage B. It can be seen from FIG. 1 that the first set of leaves Y1 and the second set of leaves Y2 are disposed oppositely to each other. Each leaf in each of the sets of leaves may move in a longitudinal direction of the leaf relative to the carriage. The longitudinal direction may be understood as a direction perpendicular to the arrangement direction of the plurality of leaves. Alternatively, the longitudinal direction may be understood as a direction proximal to or distal from another set of leaves.

For example, as shown in FIG. 1, the first set of leaves Y1 may move in the longitudinal direction of the leaf relative to the first carriage A. The second set of leaves Y2 may move in the longitudinal direction of the leaf relative to the second carriage B.

In the embodiment of the present disclosure, the drive device M1 may be a drive motor. The drive device M1 may be configured to drive the first carriage A and the second carriage B to move in the same direction synchronously. Moving in the same direction synchronously means that the moving speeds of the first carriage A and the second carriage B are equal in magnitude and the same in direction.

For example, in the multi-leaf collimator shown in FIG. 1, the drive device M1 is directly connected to the first carriage A. The second carriage B is disposed on the first carriage A. When the drive device M1 operates, the first carriage A is driven to move, and in turn, the first carriage A drives the second carriage B to move in the same direction synchronously.

In summary, the embodiments of the present disclosure provide a multi-leaf collimator. The multi-leaf collimator includes a drive device, a first carriage, a second carriage, a first set of leaves disposed on the first carriage, and a second set of leaves disposed on the second carriage. The drive device may drive the two carriages to drive the first set of leaves and the second set of leaves to move in the same direction synchronously, such that the movement of the first carriage and the second carriage can be completely synchronized. Therefore, the accuracy when the position of an irradiation field is moved with a tumor target area is improved, and the shape of the irradiation field does not change when the position of the irradiation field is moved, which achieves high accuracy and reliability of the radiotherapy. In addition, since the first carriage and the second carriage may move in the same direction synchronously, that is, the first set of leaves and the second set of leaves may move in the same direction synchronously as a whole, thereby avoiding damages to leaves due to control errors.

In an optional embodiment of the present disclosure, as shown in FIG. 1, the first carriage A may be provided with a carriage end A1, a load-bearing end A2, and a first light-transmitting hole K between the carriage end A1 and the load-bearing end A2.

The carriage end A1 is configured to mount the first set of leaves Y1. The second carriage B is disposed at the load-bearing end A2. The second carriage B is provided with the second set of leaves Y2. Correspondingly, as shown in FIG. 1, the drive device M1 is connected to the first carriage A to drive the first carriage A to move, such that the first carriage A drives the second carriage B to move in the same direction synchronously. Therefore, the position of the irradiation field may be moved correspondingly with the position of the tumor target area when the position of the tumor target area is shifted, thereby ensuring that the irradiation field can be accurately aligned with the tumor target area.

Referring to FIG. 1, the multi-leaf collimator may further include a base 10. The first carriage A is disposed on the base 10. The first carriage A is movable relative to the base 10. The base 10 is provided with a second light-transmitting hole (not shown in FIG. 1). In the embodiment of the present disclosure, an orthographic projection of the first light-transmitting hole K on the base 10 may cover an area where the second light-transmitting hole K is disposed. That is, the area of the first light-transmitting hole K is greater than or equal to that of the second light-transmitting hole, which can prevent the first carriage A from blocking rays to the second light-transmitting hole, thereby ensuring the accuracy and reliability of radiotherapy.

Optionally, as seen from FIG. 1, a cross section of the first carriage A may be L-shaped. The cross section is a cross section perpendicular to a load-bearing surface of the first carriage A and parallel to the longitudinal direction of the leaf. It can be seen from FIG. 1 that a vertical distance h1 between a load-bearing surface of the carriage end A1 and a load-bearing surface of the base 10 is equal to a vertical distance h2 between a load-bearing surface of the second carriage B and the load-bearing surface of the base 10. Therefore, it can be ensured that the first set of leaves Y1 and the second set of leaves Y2 are disposed on the same plane, and the shape of the irradiation field enclosed by the first set of leaves Y1 and the second set of leaves Y2 can be more accurate.

Optionally, as shown in FIG. 1, the multi-leaf collimator may further include a drive motor M2 disposed on the second carriage B. The drive motor M2 is configured to drive the second carriage B to move on the first carriage A.

When adjusting the position of the irradiation field, the second carriage B may be fixed on the first carriage A by a fixing component (not shown in FIG. 1), and the drive motor M2 stops operating. Therefore, it can be ensured that the second carriage B cannot move relative to the first carriage A when the drive device M1 drives the first carriage A and the second carriage B to move in the same direction synchronously, and further ensured that the shape may not change when the position of the irradiation field is moved, the reliability is enhanced.

As can be seen from FIG. 1, each leaf 01 in each set of leaves disposed on each carriage is connected to a motor 03 by a screw rod 02. The motor 03 may drive the leaf 01 connected thereto to move via the screw rod 02 connected thereto, such that the multi-leaf collimator may form a correspondingly shaped irradiation field according to different shapes of tumor target areas.

Figure 2:
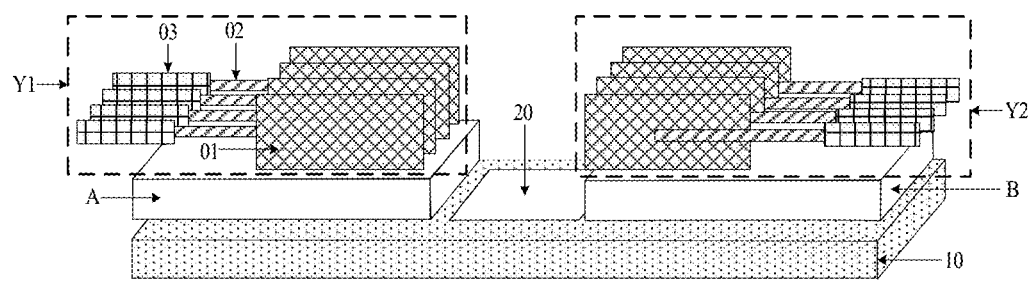
FIG. 2 is a schematic structural diagram of another multi-leaf collimator according to an embodiment of the present disclosure.

In another optional implementation of the present disclosure, as shown in FIG. 2, the multi-leaf collimator may further include a base 10 and a first differential and a second differential (not shown in FIG. 2) connected to the drive device respectively. The first carriage A and the second carriage B are disposed on the base 10 oppositely. The second light-transmitting hole 20 on the base is disposed between the first carriage A and the second carriage B. The multi-leaf collimator forms an irradiation field in the area of the second light-transmitting hole 20.

As shown in FIG. 2, the first carriage A is provided with the first set of leaves Y1. The second carriage B is provided with the second set of leaves Y2. Each leaf in each set of leaves 01 is connected to a motor 03 via a screw rod 02. The motor 03 may drive the leaf 01 connected thereto to move.

Figure 3:
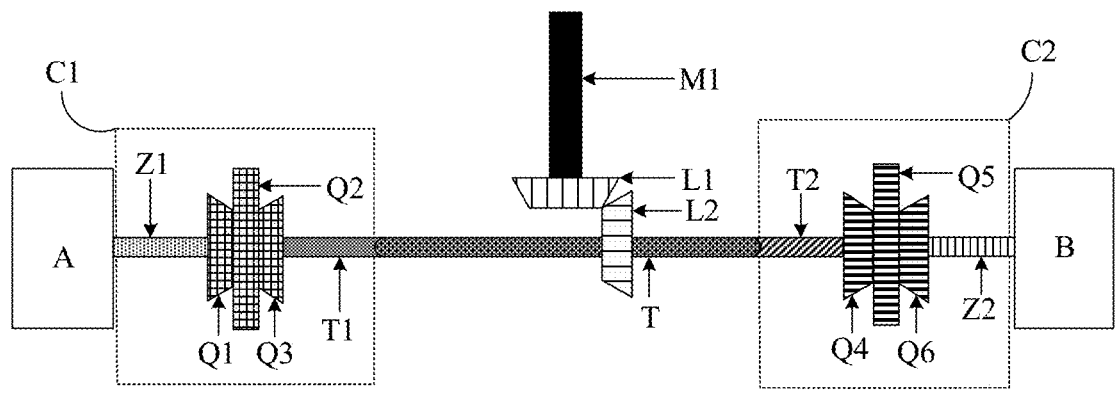
FIG. 3 is a schematic structural diagram of still another multi-leaf collimator according to an embodiment of the present disclosure.

In the embodiment of the present disclosure, as shown in FIG. 3, a first differential C1 is connected to the first carriage A. A second differential C2 is connected to the second carriage B. The drive device M1 is respectively connected to the first differential C1 and the second differential C2 to drive the first differential C1 and the second differential C2, such that the first carriage A and the second carriage B can move in the same direction synchronously.

In the embodiment of the present disclosure, since the drive device M1 can control the first differential C1 and the second differential C2 to operate at the same rotation speed, the first carriage A and the second carriage B can move in the same direction synchronously.

As shown in FIG. 3, the multi-leaf collimator further includes a main transmission shaft T and a first transmission gear L1 and a second transmission gear L2 engaged with each other. The drive device M1 is connected to the first transmission gear L1. The second transmission gear L2 is connected to the main transmission shaft T. For example, the second transmission gear L2 is sleeved on the main transmission shaft T. Moreover, one end of the main drive shaft T is connected to the first differential C1, and the other end of the main drive shaft T is connected to the second differential C2.

The drive device M1 controls the first transmission gear L1 to rotate. The first transmission gear L1 drives the second transmission gear L2 engaged therewith to rotate. Then the second transmission gear L2 drives the main transmission shaft T to rotate. In this way, the main transmission shaft T may control the first differential C1 and the second differential C2 to rotate in the same direction synchronously.

Optionally, both the first differential C1 and the second differential C2 may be planetary differentials; or both the first transmission gear L1 and the second transmission gear L2 may be bevel gears.

As shown in FIG. 3, the first differential C1 may include a first drive gear Q1, a second drive gear Q2, and a third drive gear Q3 that are engaged with each other, and a first output shaft Z1 and a first transmission shaft T1. The second drive gear Q2 is a main transmission gear of the first differential C1. Referring to FIG. 3, the second differential C2 includes a fourth drive gear Q4, a fifth drive gear Q5, and a sixth drive gear Q6 that are engaged with each other, and a second output shaft Z2 and a second transmission shaft T2. The fifth drive gear Q5 is a main transmission gear of the second differential C2.

Referring to FIG. 3, one end of the first output shaft Z1 is connected to the first carriage A, and the other end of the first output shaft Z1 is connected to the first drive gear Q1. One end of the first transmission shaft T1 is connected to the third drive gear Q3, and the other end of the first transmission shaft T1 is connected to the main transmission shaft T.

One end of the second output shaft Z2 is connected to the second carriage B, and the other end of the second output shaft Z2 is connected to the sixth drive gear Q6. One end of the second transmission shaft T2 is connected to the fourth drive gear Q4, and the other end of the second transmission shaft T2 is connected to the main transmission shaft T.

In the embodiment of the present disclosure, the drive device M1 drives the main transmission shaft T to rotate via the first transmission gear L1 and the second transmission gear L2. In turn, the main transmission shaft T drives the first transmission shaft T1 of the first differential C1 and the second transmission shaft T2 of the second differential C2 to rotate at the same rotation speed.

Further, the first transmission shaft T1 may drive the third drive gear Q3 to rotate. When the second drive gear Q2 is in a stationary state, the third drive gear Q3 in the first differential C1 drives the first drive gear Q1 to rotate. The first drive gear Q1 drives the first output shaft Z1 to rotate. The first output shaft Z1 further drives the first carriage A to move.

Correspondingly, the second transmission shaft T2 drives the fourth drive gear Q4 to rotate. When the fifth drive gear Q5 is in a stationary state, the fourth drive gear Q4 in the second differential C2 may drive the sixth drive gear Q6 to rotate. The sixth drive gear Q6 drives the second output shaft Z2 to rotate, and the second output shaft Z2 further drives the second carriage B to move.

Since the main drive shaft T can drive the first drive shaft T1 of the first differential C1 and the second drive shaft T2 of the second differential C2 to rotate at the same speed, the rotation speeds of the first drive gear Q1 and the sixth drive gear Q6 may have the same magnitude and the same direction. That is, the drive device M1 may control the moving speeds of the first carriage A and the second carriage B are equal in magnitude and opposite in direction by the first differential C1 and the second differential C2. It is ensured that the first carriage A and the second carriage B move in the same direction synchronously, thereby improving the flexibility of control.

It should be noted that the main drive shaft T may also be directly connected to the third drive gear Q3 in the first differential C1 and the fourth drive gear Q4 in the second differential C2, respectively. In this way, the main drive shaft T can directly control the third drive gear Q3 and the fourth drive gear Q4 to rotate at the same speed, which is not limited in the embodiments of the present disclosure.

Figure 4:
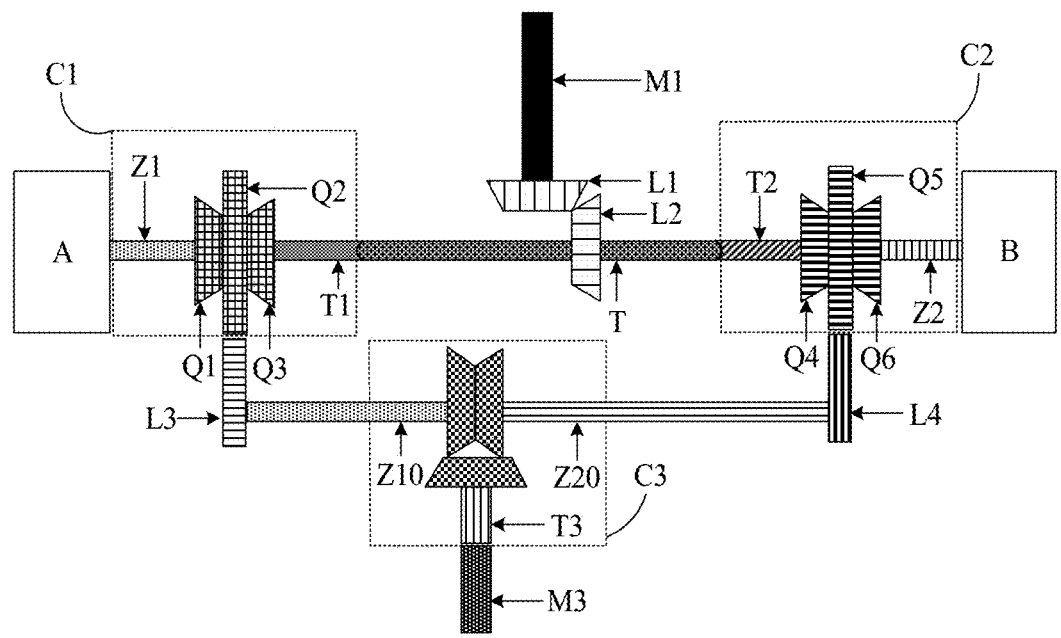
FIG. 4 is a schematic structural diagram of yet another multi-leaf collimator according to an embodiment of the present disclosure.

Optionally, as shown in FIG. 4, the multi-leaf collimator may further include a field control motor M3 and a third differential C3 connected to the field control motor M3.

Referring to FIG. 4, the third differential C3 is connected to the first differential C1 and the second differential C2 respectively. The third differential C3 may drive the first differential C1 and the second differential C2 under the driving of the field control motor M3, such that the first carriage A and the second carriage B move toward or distally from each other.

In the embodiment of the present disclosure, the field control motor M3 may control the rotation speeds of the first differential C1 and the second differential C2 to be equal and the rotation directions to be opposite, such that the first carriage A and the second carriage B may move towards or distally from each other.

Optionally, as shown in FIG. 4, the multi-leaf collimator may further include a third transmission gear L3 and a fourth transmission gear L4. A transmission shaft T3 of the third differential C3 is connected to the field control motor M3. A first output shaft Z10 of the third differential C3 is connected to the third transmission gear L3. The third transmission gear L3 is engaged with the main transmission gear in the first differential C1. The main transmission gear in the first differential C1 is the second drive gear Q2 of the first differential C1. Therefore, as shown in FIG. 4, the third transmission gear L3 is engaged with the second drive gear Q2 in the first differential C1.

A second output shaft Z20 of the third differential C3 is connected to the fourth transmission gear L4. The fourth transmission gear L4 is engaged with the main transmission gear in the second differential C2. The main transmission gear in the second differential C2 is the fifth drive gear Q5 in the second differential C2. Therefore, as shown in FIG. 4, the fourth transmission gear L4 is engaged with the fifth drive gear Q5 in the second differential C2.

In the embodiment of the present disclosure, referring to FIG. 4, the third differential C3 may also include three drive gears engaged with each other. The field control motor M3 controls the transmission shaft T3 to rotate, and the transmission shaft T3 further drive the drive gear connected thereto to rotate. In the third differential C3, the drive gear connected to the transmission shaft T3 drives the drive gear connected to its first output shaft Z10 to rotate, and drives the drive gear connected to its second output shaft Z20 to rotate. The third differential C3 control the rotation speeds of the drive gear connected to the first output shaft Z10 and the drive gear connected to the second output shaft Z20 to be equal in magnitude and opposite in direction.

Further, the drive gear connected to the first output shaft Z10 in the third differential C3 drives the first output shaft Z10 to rotate, and the first output shaft Z10 further drives the third transmission gear L3 connected to the other end thereof to rotate. Then, the third transmission gear L3 drives the second drive gear Q2 to rotate. Correspondingly, the drive gear connected to the second output shaft Z20 in the third differential C3 drives the second output shaft Z20 to rotate. The second output shaft Z20 then drives the fourth transmission gear L4 connected to the other end thereof to rotate. The fourth transmission gear L4 drives the fifth drive gear Q5 to rotate.

Further, the second drive gear Q2 drives the first drive gear Q1 and the third drive gear Q3 to rotate. The first drive gear Q1 drives the first output shaft Z1 to rotate. The first output shaft Z1 drives the first carriage A to move. Correspondingly, the fifth drive gear Q5 drives the fourth drive gear Q4 and the sixth drive gear Q6 to rotate. The sixth drive gear Q6 then drives the second output shaft Z2 to rotate. The second output shaft Z2 drives the second carriage B to move.

Under the control of the field control motor M3 and the third differential C3, the rotation speeds of the first drive gear Q1 and the sixth drive gear Q6 are equal in magnitude and opposite in direction. That is, the field control motor M3 controls the moving speeds of the first carriage A and the second carriage B to be equal in magnitude and opposite in direction by the third differential C3.

When adjusting the shape of the radiation field, the field control motor M3 may control the moving speeds of the first carriage A and the second carriage B to be equal in magnitude and opposite in direction by the third differential C3. As a result, the first carriage A and the second carriage B move toward or distally from each other, and the control flexibility is relatively high.

In summary, the embodiments of the present disclosure provide a multi-leaf collimator. The multi-leaf collimator includes a drive device, a first carriage, a second carriage, a first set of leaves disposed on the first carriage, and a second set of leaves disposed on the second carriage. The drive device may drive the two carriages to drive the first set of leaves and the second set of leaves to move in the same direction synchronously, such that the movement of the first carriage and the second carriage can be completely synchronized. Therefore, the accuracy when the position of an irradiation field is moved with a tumor target area is improved, and the shape of the irradiation field does not change when the position of the irradiation field is moved, which results in high accuracy and reliability of the radiotherapy. In addition, since the first carriage and the second carriage may move in the same direction synchronously, that is, the first set of leaves and the second set of leaves may move in the same direction synchronously as a whole, thereby avoiding damages to leaves due to control errors.

An embodiment of the present disclosure provides a radiotherapy equipment, which may include a multi-leaf collimator as shown in any one of FIGS. 1 to 4. When breathing of a patient affects the position of the tumor target area, the multi-leaf collimator can make the position of an irradiation field track the position of a tumor target area, thereby ensuring that rays emitted from a radiation source of the radiotherapy equipment can accurately irradiate the tumor target area through the radiation field. The radiotherapy equipment achieves high tracking accuracy and good reliability, and can realize the function of tracking the tumor target area without increasing the drive load of the leaf motor.

Those skilled in the art will easily think of other embodiments of the present disclosure after considering the specification and practicing the application disclosed herein. This application is intended to cover any variations, uses, or adaptive changes of the present disclosure. These variations, uses, or adaptive changes follow the general principles of the present disclosure and include common knowledge or conventional technical means in the technical field which are not disclosed in the present disclosure. The description and the embodiments are only regarded as examples, and the true scope and spirit of the present disclosure are pointed out by the claims.

It should be understood that the present disclosure is not limited to the precise structure that has been described above and shown in the drawings, and various modifications and changes may be made without departing from the scope of the present disclosure. The scope of the present disclosure is defined by the appended claims.

What is claimed is:

1. A multi-leaf collimator, comprising:
a first carriage, a second carriage, a drive device, a first set of leaves disposed on the first carriage, and a second set of leaves disposed on the second carriage, wherein
the first set of leaves and the second set of leaves are disposed oppositely to each other, and each leaf in each of the sets of leaves is movable relative to each respective carriage; and
the drive device is configured to drive the first carriage and the second carriage to move in the same direction synchronously, wherein
the first carriage is provided with a carriage end, a load-bearing end, and a first light-transmitting hole between the carriage end and the load-bearing end; wherein
the carriage end is configured to mount the first set of leaves;
the second carriage is disposed at the load-bearing end; and
the drive device is connected to the first carriage and configured to drive the first carriage to move, such that the first carriage drives the second carriage to move in the same direction synchronously.

2. The multi-leaf collimator according to claim 1, further comprising a base; wherein
the first carriage is disposed on the base, and the base is provided with a second light-transmitting hole; and
an orthographic projection of the first light-transmitting hole on the base covers an area where the second light-transmitting hole is disposed.

3. The multi-leaf collimator according to claim 1, further comprising a drive motor disposed on the second carriage; wherein
the drive motor is configured to drive the second carriage to move.

4. A multi-leaf collimator, comprising:
a first carriage, a second carriage, a drive device, a first set of leaves disposed on the first carriage, and a second set of leaves disposed on the second carriage, wherein
the first set of leaves and the second set of leaves are disposed oppositely to each other, and each leaf in each of the sets of leaves is movable relative to each respective carriage; and
the drive device is configured to drive the first carriage and the second carriage to move in the same direction synchronously,
wherein the first carriage and the second carriage are disposed oppositely to each other, and the multi-leaf collimator further comprises a first differential and a second differential; wherein
the first differential is connected to the first carriage, and the second differential is connected to the second carriage; and
the drive device is connected to the first differential and the second differential respectively, and configured to drive the first differential and the second differential such that the first carriage and the second carriage move in the same direction synchronously, wherein
the multi-leaf collimator further comprises a main drive shaft, and a first transmission gear and a second transmission gear that are engaged with each other; wherein
the drive device is connected to the first transmission gear, and the second transmission gear is sleeved on the main drive shaft; and
one end of the main drive shaft is connected to the first differential, and the other end of the main drive shaft is connected to the second differential.

5. The multi-leaf collimator according to claim 4, wherein the multi-leaf collimator meets at least one of the following conditions:
both the first differential and the second differential are planetary differentials; and
both the first transmission gear and the second transmission gear are bevel gears.

6. The multi-leaf collimator according to claim 4, further comprising: a field control motor, and a third differential connected to the field control motor; wherein
the third differential is connected to the first differential and the second differential respectively, and configured to drive the first differential and the second differential under the drive of the field control motor, such that the first carriage and the second carriage move toward or distally from each other.

7. The multi-leaf collimator according to claim 6, further comprising: a third transmission gear and a fourth transmission gear; wherein
a transmission shaft of the third differential is connected to the field control motor;
a first output shaft of the third differential is connected to the third transmission gear, and the third transmission gear is engaged with a main transmission gear in the first differential; and
a second output shaft of the third differential is connected to the fourth transmission gear, and the fourth transmission gear is engaged with a main transmission gear in the second differential.

8. A radiotherapy equipment, comprising:
a radiation source; and
a multi-leaf collimator, wherein the multi-leaf collimator comprises: a first carriage, a second carriage, a drive device, a first set of leaves disposed on the first carriage, and a second set of leaves disposed on the second carriage, wherein the first set of leaves and the second set of leaves are disposed oppositely to each other, and each leaf in each of the sets of leaves is movable relative to each respective carriage; and the drive device is configured to drive the first carriage and the second carriage to move in the same direction synchronously, wherein the first carriage is provided with a carriage end, a load-bearing end, and a first light-transmitting hole between the carriage end and the load-bearing end; wherein the carriage end is configured to mount the first set of leaves;

the second carriage is disposed at the load-bearing end; and the drive device is connected to the first carriage and configured to drive the first carriage to move, such that the first carriage drives the second carriage to move in the same direction synchronously.

9. The radiotherapy equipment according to claim 8, wherein the multi-leaf collimator further comprises a base; wherein the first carriage is disposed on the base, and the base is provided with a second light-transmitting hole; and an orthographic projection of the first light-transmitting hole on the base covers an area where the second light-transmitting hole is disposed.

10. The radiotherapy equipment according to claim 8, wherein the multi-leaf collimator further comprises a drive motor disposed on the second carriage; wherein the drive motor is configured to drive the second carriage to move.

11. The multi-leaf collimator according to claim 1, further comprising motors connected to leaves in each set of leaves in a one-to-one correspondence; wherein each of the motors is configured to drive the leaf as connected to move relative to each respective carriage.

12. The radiotherapy equipment according to claim 8, wherein the multi-leaf collimator further comprises: motors connected to leaves in each set of leaves in a one-to-one correspondence; wherein each of the motors is configured to drive the leaf as connected to move relative to each respective carriage.

* * * * *